United States Patent [19]

Meissner

[11] Patent Number: 5,135,468
[45] Date of Patent: Aug. 4, 1992

[54] METHOD AND APPARATUS OF VARYING THE BRAIN STATE OF A PERSON BY MEANS OF AN AUDIO SIGNAL

[76] Inventor: Juergen P. Meissner, 551 Route 10, Randolph, N.J. 07869

[21] Appl. No.: 561,776

[22] Filed: Aug. 2, 1990

[51] Int. Cl.$^5$ ............................................. A61M 21/00
[52] U.S. Cl. ......................................................... 600/28
[58] Field of Search ..................................... 600/26–28; 128/731–732

[56] References Cited

U.S. PATENT DOCUMENTS

| 4,335,710 | 6/1982 | Williamson | 600/28 |
| 4,418,687 | 12/1983 | Matsumoto et al. | 600/26 |
| 5,036,858 | 8/1991 | Carter et al. | 600/27 |

FOREIGN PATENT DOCUMENTS

| 3626385 | 2/1988 | Fed. Rep. of Germany | 600/28 |
| 2165985 | 4/1986 | United Kingdom | 600/28 |

OTHER PUBLICATIONS

"A New Prescription: Mind over Malady" by Rob Welchsler, Discover Magazine, Feb. 1987.
"Physiology of Meditation", Scientific American, by Robert Keith Wallace and Herbert Bensen, Feb. 1972, vol. 226, No. 2, pp. 84–90.
Adler's Physiology of the Eye, Chapter 13, "Visual Pathways", p. 444.
"The Monroe Institute's Hemi-Sync Process—A Theoretical Perspective" by F. Holmes Atwater, Aug. 1988.
"Data Transformation explains the Basics of Neural Networks" by Doug Conner, EDN, May 12, 1988.
"The Mind within the Brain" by Gina Maranto, Discover Magazine, May, 1984, pp. 34–43.

*Primary Examiner*—Lee S. Cohen
*Assistant Examiner*—John P. Lacyk
*Attorney, Agent, or Firm*—Richard M. Goldberg

[57] ABSTRACT

A method of varying the brain state of a person includes the steps of supplying the first audio signal to one ear of the person, supplying a second audio signal to the other ear of the person, and substantially continuously varying the frequency of at least one of the first and second audio signals to vary the brain state of the person.

57 Claims, 9 Drawing Sheets

METHOD AND APPARATUS OF VARYING THE BRAIN STATE OF A PERSON BY MEANS OF AN AUDIO SIGNAL

BACKGROUND OF THE INVENTION

This invention relates generally to the human brain, and more particularly, to modification of the state of being of the human brain by use of an audio signal.

It is known that the brain operates at different frequencies. These frequencies are generally classified in different regions, for example, the Delta, Theta, Alpha, and Beta brain states. Specifically, the lowest frequency is the Delta brain state which is the sleep state and which is believed to operate in a 2 to 4 Hz region. The next state is a Theta state which is a deep meditative state and operates in the region of 4 to 7 Hz. After the Theta state, there is the Alpha state which is a normal non-active wakeful or idle state and operates in the 7 to 14 Hz region. Finally, the Beta state is the normal active state and operates in the region greater than 14 Hz and possibly as high as 40 Hz.

In many instances, a person is operating in one brain state and desires to be in another brain state. For example, people with insomnia have difficulty entering the lower brain states to fall asleep. In the opposite regard, it may be difficult for people to wake up completely and enter a normal active state in the Beta region.

Many chemicals, legal and illegal substances, such as coffee, nicotine, alcohol, tranquilizers, sleeping pills, amphetamines, and the like, are traditionally used to create these states. The side effects and possible addiction to these substances is well-known.

Therefore, the need and desire is very strong and there has been a great search for techniques and/or external stimuli which can vary the brain state. Much has been written about the benefits of relaxation and stress reduction. Stress has been shown to contribute to heart attacks, and is known to suppress the normal operation of the immune system, thus leaving the body vulnerable to attack from many serious illnesses. See "A New Prescription: Mind over Malady" by Rob Welchsler, Discover Magazine, February, 1987.

Another such article is The "Physiology of Meditation", Scientific American, by Robert Keith Wallace and Herbert Bensen, February, 1972, Volume 226, No. 2, Pages 84-90. This article discusses the use of transcendental meditation for varying the brain state, and discusses the various tests for determining the change in brain states, including skin resistance to an electric current, heartbeat, the rate and volume of respiration and an electroencephalogram pattern.

Different approaches have been made with respect to varying the brain state of a person. For example, various audio systems are commercially sold using subliminal messages in order to coax the brain into a different state. Examples of such systems are those sold by Zygon, 1420 Northwest Gilman Boulevard, Suite 2655, Issaquah, Wash. 98027; Outer Skin Performance, P.O. Box 7597, Beverly Hills, Calif. 90212-7597; and Effective Learning Systems, Inc., 5221 Industrial Boulevard, Edina, Minn. 55435. However, such subliminal messages, even when coupled with environmental sound and/or music, as is conventional, are insufficient to vary the brain state of a person.

It has also been suggested that the brain state of a person can be changed or driven by exposing the eye to flickering lights. Specifically, at a certain rate of flicker, it is suggested that the Alpha rhythm changes from its original rhythm to that of the flickering light. See, for example, Adler's Physiology of the Eye, Chapter 13, "Visual Pathways", Page 444. However, this brute-force method of changing the brain state has never been put into practice and is rarely successful.

In like manner, it has been suggested that the use of an audio signal in a similar manner will produce a similar result. This suggestion has been made in an article "The Monroe Institute's Hemi-Sync Process—A Theoretical Perspective" by F. Holmes Atwater, August, 1988. As discussed therein, the author indicates that a beat frequency can be produced inside of the brain by supplying signals of different frequencies to the two ears of a person. As a result, binaural beats are produced and are perceived by the brain as a result of the interaction of auditory signals within the brain. Such binaural beats are not produced outside of the brain as a result of the two audio signals of different frequencies. In a sense, the binaural beats are similar to beat frequency oscillations produced by a heterodyne effect, but occurring within the brain itself. However, the article discusses the use of such binaural beats in a strobe-type manner. In other words, if the brain is operating at one frequency, binaural beats of a fixed frequency are produced within the brain so as to entice the brain to change its frequency to that of the binaural beats and thereby change the brain state. However, as discussed above, this brute-force method is rarely successful.

It is also known that there are methods of attaching electrodes to the brain and inducing various stimuli. For example, there is an "electro sleep" method where a mild current is passed through the temples. This method is not approved in this country. "Electro shock" treatments use the same input, but with larger currents. Another treatment induces an alternating current of various frequencies to electrodes attached behind the ears. These methods are invasive and need to be administered by a physician.

OBJECTS AND SUMMARY OF THE INVENTION

Accordingly, it is an object of the present invention to provide a method and apparatus of varying the brain state of a person using an audio signal, that overcomes the aforementioned problems with the prior art.

It is another object of the present invention to provide a method and apparatus of varying the brain state of a person using an audio signal, that produces continuously varying binaural beats within the brain.

It is still another object of the present invention to provide a method and apparatus of varying the brain state of a person using continuously varying frequencies that phase lock the brain thereto so as to change the brain-wave frequency, and thereby, the brain state of a person.

It is yet another object of the present invention to provide a method and apparatus for varying the brain state of a person using an audio signal, that can provide either relaxation, sleep or increased brain activity.

It is a further object of the present invention to provide a method and apparatus for varying the brain state of a person using an audio signal, that is non-invasive.

It is a still further object of the present invention to provide a method and apparatus for varying the brain state of a person using an audio signal, that can be used by a person during normal, daily activities without the requirement of a physician.

In accordance with an aspect of the present invention, apparatus for varying the brain state of a person, includes means for producing a first audio signal to be supplied to one ear of the person; means for producing a second audio signal to be supplied to the other ear of the person; and means for substantially continuously varying the frequency of both of the first and second audio signals only in a first direction in a range of approximately 0–60 Hz and in a substantially identical manner, so as to vary the brain state of the person.

In accordance with another aspect of the present invention, a method for varying the brain state of a person, includes the steps of producing a first audio signal to be supplied to one ear of the person; producing a second audio signal to be supplied to the other ear of the person; and substantially continuously varying the frequency of both of the first and second audio signals only in a first direction in a range of approximately 0–60 Hz and in a substantially identical manner, so as to vary the brain state of the person.

In accordance with still another aspect of the present invention, apparatus for varying the brain state of a person, includes signal supply means for producing a first frequency signal used to generate a first audio signal to be supplied to one ear of the person, and a second frequency signal used to generate a second audio signal to be supplied to the other ear of the person, such that the frequency of both of the generated first and second audio signals substantially continuously vary only in a first direction in a range of approximately 0–60 Hz and in a substantially identical manner, so as to vary the brain state of the person.

In accordance with yet another aspect of the present invention, apparatus for varying the brain state of a person, includes means for producing a first audio signal to be supplied to one ear of the person; means for producing a second audio signal to be supplied to the other ear of the person; and means for substantially continuously varying the frequency of at least one of the first and second audio signals such that substantially continuously varying binaural beats are produced in the brain of the person when the first and second audio signals are supplied to the first and second ears, respectively.

In accordance with a further aspect of the present invention, a method for varying the brain state of a person, includes the steps of producing a first audio signal to be supplied to one ear of the person; producing a second audio signal to be supplied to the other ear of the person; and substantially continuously varying the frequency of at least one of the first and second audio signals such that substantially continuously varying binaural beats are produced in the brain of the person when the first and second audio signals are supplied to the first and second ears, respectively.

In accordance with a still further aspect of the present invention, apparatus for varying the brain state of a person, includes signal supply means for producing a first frequency signal used to generate a first audio signal to be supplied to one ear of the person, and a second frequency signal used to generate a second audio signal to be supplied to the other ear of the person, such that the frequency of at least one of the first and second audio signals is substantially continuously varied such that substantially continuously varying binaural beats are produced in the brain of the person when the first and second audio signals are supplied to the first and second ears, respectively, so as to vary the brain state of the person.

The above and other objects, features and advantages of the present invention will become readily apparent from the following detailed description thereof which is to be read in connection with the accompanying drawings.

DETAILED DESCRIPTION OF THE PREFERRED EMBODIMENTS

Figure 1:
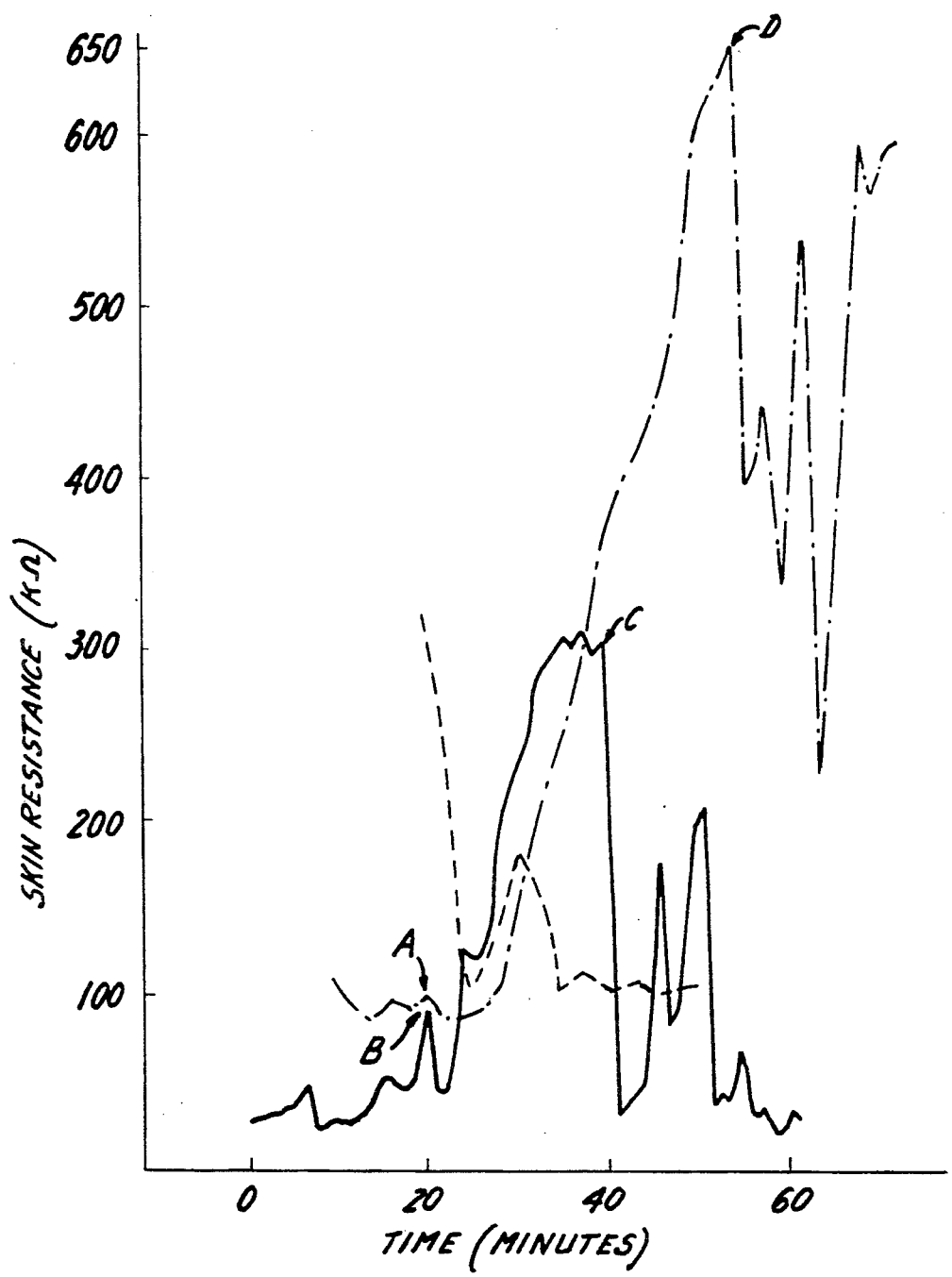
FIG. 1 is a graphical diagram of skin resistance versus time for the RELAX mode in comparison with the prior art.

The present invention is primarily separated into three types of variation of brain activity.

The first embodiment is a RELAX embodiment which lowers the frequency of the brain waves, although not into the sleep region, in order to relax the person.

In the second SLEEP embodiment, the brain state is changed so that the brain waves thereof are lowered. This embodiment is ideally suited to bring a person from the normal Alpha state to the sleep or Delta region.

The third UP embodiment is to the contrary and is particularly suited for raising the brain-wave frequency to a higher state, for example, from an Alpha or lower Beta state to a higher Beta state. It has been found that this embodiment is particularly suited for increasing performance during sports activities.

In all of the embodiments which will be discussed hereinafter in more detail, it is essential that a continuously varying, audio signal be produced in which the frequency thereof or binaural beats produced thereby passes through the then operating brain-wave frequency, or is an integral multiple thereof, of the person in order to lock onto and change the brain-wave frequency.

With the above in mind, it is noted that the human brain is so complex that its operation is still not completely understand. Even though there is a basic understanding of neurons and nerve impulses, understanding of all the intricate interconnections and functions is still a long way off. In this regard, modern computers, such as in neural networks, parallel processing and artificial intelligence, are beginning to copy some of the brain functions. Some complex neural networks and learning algorithms are being implemented in software using existing serial mode digital computers. See the article "Data Transformation explains the Basics of Neural Networks" by Doug Conner, EDN. May 12, 1988. As proud as man is of his success, it must be realized that only a very small capability of the human brain has been achieved, even using the largest computer with the best programming.

However, there are some simple external indicators that let us infer as to what the central processing unit (the brain) is attempting to do. For example, the presence of perspiration indicates excessive temperature. These indicators will be discussed hereinafter with respect to the particular embodiments.

RELAX EMBODIMENT

As background, and using a computer stress analogy, in modern multi-tasking computer systems, it is found that although the computer system can perform many concurrent programs, and many seemingly parallel tasks, a point is reached where each program utilizes the central processing unit to such an extent that a very significant slowdown occurs. One such example is a word processor that is printing a document in the background and which becomes extremely slow and sluggish in response to the keyboard inputs. More sophisticated programs will stop printing and service the keyboard as the first priority. With multi-tasking, each program has its own level of priority, but a point is soon reached where all programs will be slowed to a point of inefficiency. One way to overcome this problem is to review what programs are running and shut down the ones that are not necessary. The simplest method is to turn power off or reboot and start from scratch, loading only those programs that are needed. With the human computer, that is, the brain, this overloading occurs when a person tries to do too many things at the same time. The result is stress, loss of efficiency and errors. When stress is allowed to continue, the health and well-being of the person is affected. It is important therefore to occasionally "reboot" the brain computer. This is the function that the RELAX embodiment performs.

It is known that telling a stressed person to relax is rarely effective. Even when the person knows that he must try to relax, he usually cannot. Meditation and other relaxation methods seldom work with this type of person. Worrying about being stressed makes the person more stressed, producing a vicious cycle. The task is to figure out how to break into this cycle or how to "reboot".

To use the computer analogy, a person has temporary storage and permanent storage. The computer uses RAM (random access memory) computer chips for the temporary storage of data and floppy discs or the like to store permanent records. It is known that the brain has these functions also, but it is not know how this is accomplished.

In the computer system, there is a reset button that will erase all of the temporary storage area and not effect the permanent storage (discs). It would be useful to have a reset button for the brain. Since there is none, another path must be provided to produce this effect.

The computer chips used for the RAM function are either static or dynamic. The advantages of dynamic RAM is lower power consumption and much higher storage capability per package. The disadvantage is that the computer must provide a refresh pulse every few milliseconds, otherwise these chips will forget. Some early computer systems used the CPU to refresh the RAM. If the computer was kept busy with some external input, the CPU would not be able to refresh the RAM, thus causing the inadvertent loss of the temporary memory. The brain appears to work in this manner and needs to be refreshed to remember. See "The Mind within the Brain" by Gina Maranto, Discover Magazine, May, 1984, pages 34–43. The answer then is to keep the brain too busy with some external input so that it cannot refresh, and therefore forgets. The RELAX process is designed to saturate and overload the audio input channels not with sound, but information. The audio input makes the brain think that there are many moving targets that must be tracked. Specifically, as will be discussed hereinafter, in the RELAX embodiment, continuously varying binaural beats are produced in the brain.

In order to understand this embodiment, some background information is necessary with respect to the following analogy. The brain is similar to a dynamic random access memory (RAM). In such case, the brain must constantly refresh itself in order to remember. During high-stress periods, too much information is being refreshed. It is therefore necessary to eliminate undesirable information and thereby relieve the stress of the person. The audio signal supplied during the RELAX embodiment pushes the unwanted information into the background so that the brain does not constantly refresh the same. As a result, the brain concentrates on the external audio signal and does not refresh the unwanted information. Therefore, the unwanted information is lost so as to relieve the tension. At the same time, the brain-wave frequency is lowered.

Generally, the binaural beat frequency that the brain can detect, ranges from approximately 0 to 30 Hz. As stated in the Atwater article, the highest binaural frequency that the brain can detect is 30 Hz. Further, according to the Fletcher-Munson curve, the ear has the greatest sensitivity at 3000 Hz. However, this frequency is not pleasant to listen to, and a frequency of 100 Hz is too low to provide a good modulation index. The frequency of 200 Hz is a compromise between sensitivity and pleasing sounds.

In accordance with a preferred embodiment of the present invention, a constant frequency of 200 Hz audio signal is supplied to the left ear and a continuously varying audio signal having a frequency which ranges from 230 Hz and decreases to 200 Hz is applied to the right ear. As a result, binaural beats starting at 30 Hz are produced in the brain and reduce down to 0 Hz. The signals are then toggled and the constant frequency is applied to the right ear and the continuously varying audio signal is applied to the left ear. The binaural beats still vary from 30 Hz down to 0 Hz, but the opposite brain hemisphere is tracking the variable frequency. This toggling is done so that each hemisphere is treated the same and the frequencies of the two hemispheres will be synchronized.

During the next scan, a constant frequency audio signal of 200 Hz is applied to the left ear while an audio signal having a frequency which continuously varies from 229 Hz to 200 Hz is applied to the right ear so as to produce binaural beat frequencies ranging from 29 Hz to 0 Hz. During each scan, the highest frequency is decreased by one Hz and then toggled to the other ear. As the range of frequency is reduced, the frequency/- second slope is also reduced so as to spend more time at each frequency.

Importantly, with the RELAX embodiment, the frequency is decreased substantially continuously as defined herein. For example, the change in frequency can be computer generated so as to change by a maximum of approximately 0.001 Hz/sec. Such variation is so small as to effectively be continuous.

With the RELAX mode, the absolute amplitude is preferably greater than 60 db, and is preferably 100 dB. The absolute amplitude is constant and the louder the amplitude, the better. In effect, in the relax mode, the absolute amplitude approaches the threshold of comfort. It has been found that low level amplitudes take longer to take effect. There is no amplitude modulation in the relax embodiment.

Further, in the RELAX embodiment, there is a continuous phase change from 0 degrees to 360 degrees, which appears to the person as if he is revolving or rotating, or the person may sense that the source of the sound is rotating around him or passing from left to right and then from right to left. The effect, at least initially, is somewhat of a loss of equilibrium due to overloading of the brain sensors.

Tests have shown that some people respond to the RELAX process in as little 1–5 minutes while others require 20 or more minutes. In cases of high stress, two passes are necessary, generally taking 30 to 40 minutes. Further, the frequencies and other characteristics of the audio signals can be customized for each individual.

The different changing beats make the brain think that there are a plurality of targets moving around so as to maintain the attention span of the brain. If a constant frequency, as in the prior art, is supplied to both ears, the brain would identify and ignore such frequency and thereby not lock onto the same.

The RELAX mode thereby provides a two-fold function. First, it eliminates unnecessary background information in the brain, that is, prevents refreshing of the same. Secondly, since the binaural beats are continuously reduced, they entice a reduction of the brain's operating frequency to a more relaxed lower brain state.

It is noted that the mixing process does not occur at audio frequencies in a physical sound pressure sense, but rather, it is after the ears have converted the sound to neurological traffic that the brain compares left and right inputs. In effect, the binaural beats create a neurological traffic jam between the right and left hemispheres.

As discussed in the aforementioned Scientific American article, there are many measurable external factors that can be used to determine some of the brain states. The most easily measured factor is the skin resistance and temperature. With respect to skin resistance, there appears to be a correlation between skin resistance and the activity of the sympathetic nervous system. Skin temperature appears to be a secondary effect of the activity of the sympathetic nervous system, that is, the vasoconstriction of the blood vessels. For example, it is known that high levels of stress will make the fingertips and feet become significantly colder. However during good sleep, and therefore low stress, the head, finger and toe temperatures will be essentially equal.

Figure 2:
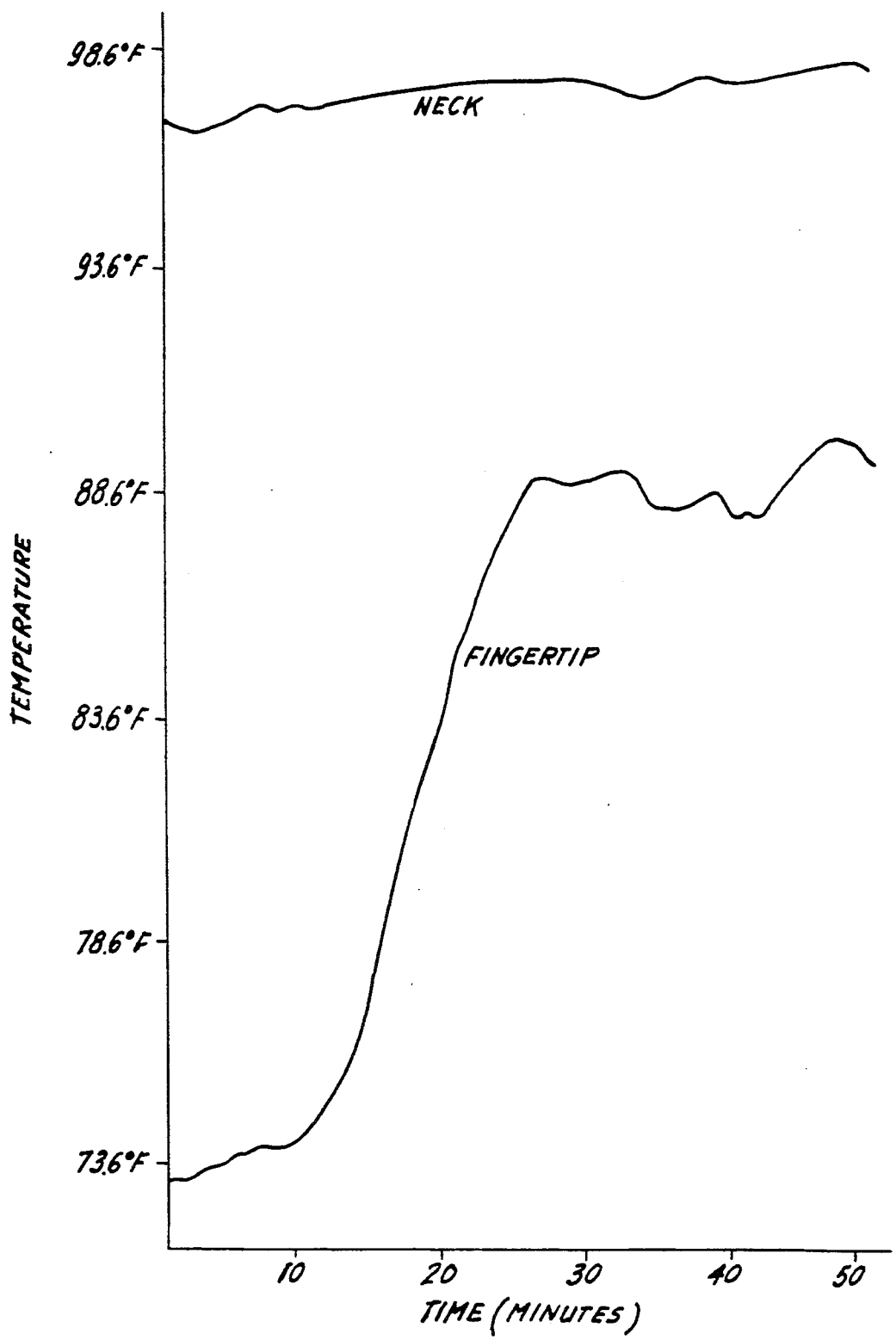
FIG. 2 is a graphical diagram of temperature versus time for the RELAX mode.

As shown by the dot-dash lines in FIGS. 1 and 2, both skin resistance and body temperature change to indicate a more relaxed state of mind. Also shown by the solid line in FIG. 1 is a comparable signal scaled down accordingly for a meditative state from the aforementioned Scientific American article. It is clear from FIG. 1 that the RELAX embodiment of the present invention produces a more relaxed state than meditation in a shorter period of time, and that the results thereof last longer after the stimulus is removed. Further, the present invention, as shown in FIG. 1, produces a more relaxed state than the known prior art where a constant frequency signal is used (the dashed line in FIG. 1). In FIG. 1, point A represents the point where the RELAX embodiment is first applied; point B represents the point where meditation begins according to the Scientific American article; point C represents the point where meditation ends; and point D represents the point where the RELAX audio signal is terminated. The dashed line shows the curve where a constant frequency is applied according to the prior art. As shown in FIG. 2, the fingertip temperature rises to approach normal body temperature.

The above audio signals can be produced in a plurality of ways. For example, an audio signal generator can be used to produce the audio signals and listened to through headphones. A computer program can be written to produce the required sound. Alternatively, analog operational amplifiers and other integrated circuitry can be provided in conjunction with a set of headphones to produce such audio signals. These signals may be recorded on a magnetic tape which the person listens to through a set of earphones. Headphones are necessary because otherwise the beat frequency would be produced in the air between the two speakers. This would produce audible beat notes, but would not produce the binaural beats within the brain.

Figure 3:
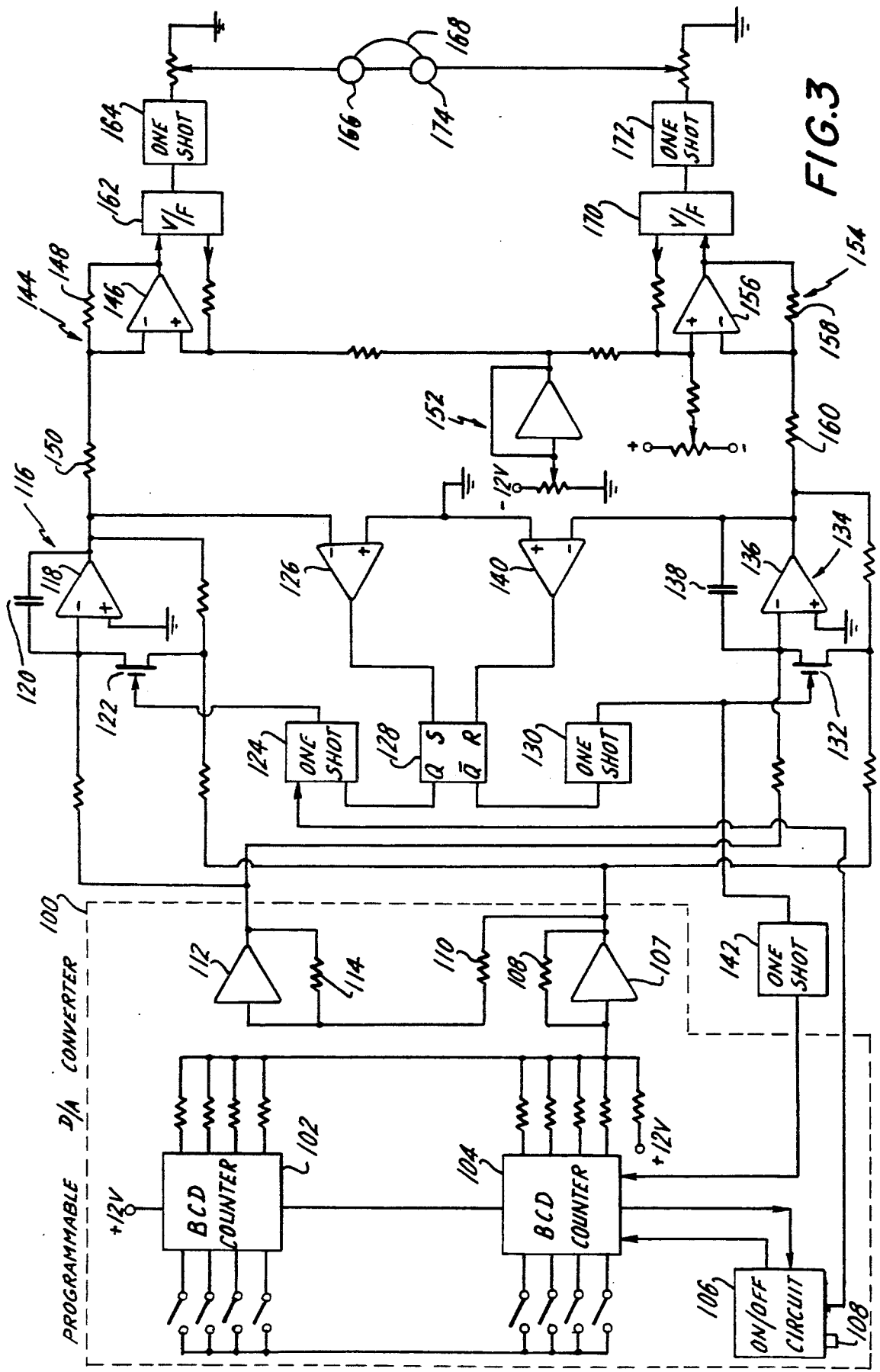
FIG. 3 is a block-circuit wiring diagram for producing audio signals for the RELAX mode.

Referring now to FIG. 3, a circuit for producing the change in audio signals includes a programmable digital-to-analog (D/A) converter 100 comprised of a BCD ladder formed by two BCD counters 102 and 104. ON/OFF circuit 106 is connected to one input of BCD counter 104 and has a start button associated therewith in order to start operation of the circuit. When the count of the BCD ladder goes below zero, BCD counter 104 supplies a signal to ON/OFF circuit so as to stop the operation.

The output of BCD counter 104 is supplied to an amplifier 107 having a feedback resistor 108. The output from amplifier 107 is a DC voltage proportional to the count and forms a maximum beat frequency signal. The output from amplifier 107 is supplied through a resistor 110 to the input of another amplifier 112 having a feedback resistor 114, and the output of amplifier 112 constitutes an inverse signal of the output of amplifier 107, which corresponds to a slope or Hz/sec. signal. Thus, when start button 108 is depressed, the BCD ladder, which forms a down counter, is loaded with the number 30 so as to count down therefrom and the output from amplifier 107 corresponds to such count.

The output from amplifier 107 is supplied to a first integrator 116 formed by an amplifier 118 and a capacitor 120 in parallel therewith. Integrator 116 is supplied with the output signal from amplifier 107 corresponding to the count from the BCD ladder. For example, a count of 30 may correspond to a voltage of +3V such that integrator 116 is loaded with the 3V signal and ramps down to 0V. In addition, the input of amplifier 118 is connected with a switching FET 122 having its input connected to a one-shot or monostable multivibrator 124. One shot 124 has one input connected with ON/OFF circuit 106 so as to be activated upon depression of start button 108. In this manner, upon depression of start button 108, the BCD ladder supplies a signal through amplifier 107 to amplifier 118 of first integrator 116, and first integrator 116 is enabled by one shot 124 simultaneously therewith to start ramping down the signal. The output from first integrator 116 is supplied to the inverting input of a first comparator 126, the non-inverting input being connected to ground. Accordingly, when first integrator 116 ramps down to 0V, first comparator 126 supplies a signal to the set input S of a RS flip-flop 128 which, in turn, supplies an appropriate signal to a one-shot 130 that activates a switching FET 132 to enable operation of a second integrator 134 formed by an amplifier 136 and a capacitor 138 in parallel therewith. At the same time, a signal is supplied to one-shot 124 so as to control switching FET 122 to disable first integrator 116. As a result, the output signal from amplifier 112 which is the inverted signal from amplifier 106, is supplied to amplifier 136 of second integrator 134 which ramps down the signal from Δ3V to 0V, whereupon second comparator 134 resets flip-flop 128 through a second comparator 140. At this time, one-shot 130 is activated to disable second integrator 134 and enable first integrator 116. At the same time, one-shot 130 supplies a signal to another one-shot 142 which, in turn, supplies a signal to BCD counter 104 to decrement the signal and thereby step down the counter for the next cycle.

During the above operations, the output signal, during activation of first integrator 116, is supplied to a differential amplifier 144 that flips the voltage. Specifically, the output from first integrator 116 is from 0V to 3V, and first differential amplifier 144 flips the voltage so as to operate from 12V to 0V. In this manner, first differential amplifier 144 includes an amplifier 146 along with a feedback resistor 148. The output signal from amplifier 118 of first integrator 116 is supplied through a resistor 150 to the inverting input of amplifier 146. The non-inverting input of amplifier 146 is supplied with a constant voltage from a voltage setting circuit 152 which sets the voltage for a constant carrier frequency of 200 Hz.

In like manner, a second differential amplifier 154 is provided and is formed by an amplifier 156 along with a feedback resistor 158, with the inverting input of amplifier 156 being connected through a resistor 160 to the output of amplifier 136 of second integrator 134. The non-inverting input of amplifier 156 is connected to voltage setting circuit 152.

The output from first differential amplifier 146 is supplied to a voltage-to-frequency (V/F) converter 162 which converts the voltage supplied thereto to a frequency. For example, 12V would correspond to 0 Hz and 0V would correspond to a maximum frequency. The output from V/F converter 162 is supplied to a one-shot 164 which, in turn, supplies an output signal to the left ear 166 of headphones 168. In like manner, the output signal from second differential amplifier 156 is supplied through a V/F converter 170 and a one-shot 172 to the right ear 174 of headphones 168. With such circuitry, the aforementioned signal in the RELAX embodiment is produced.

It will also be appreciated that the audio signal in accordance with the present invention can be computer generated, for example, as shown by the following computer program:

START1:

```
STARTFREQ = 31
ENDFREQ = 0
DURATION = 2
STEPFREQ = .0045
CENTERFREQ = 200.001
B=STARTFREQ + CENTERFREQ
C=ENDFREQ + CENTERFREQ
D=DURATION
S=STEPFREQ
F=CENTERFREQ
   FOR X=1 TO STARTFREQ
      S=STEPFREQ * ( STARTFREQ -X)
      B=STARTFREQ+CENTERFREQ
      B=B-X
         GOSUB DOWNFREQRIGHT
         DELAY1: FOR T=1 TO 1000 : NEXT T
      S=STEPFREQ * ( STARTFREQ -X)
      B=STARTFREQ+CENTERFREQ
      B=B-X
         GOSUB DOWNFREQLEFT
         DELAY1: FOR T=1 TO 1000 : NEXT T
   NEXT X
STOP
DOWNFREQLEFT: B=B-S: SOUND B,D,200,1: SOUND F,D,255,0:
SOUND RESUME: IF B>C THEN GOTO DOWNFREQLEFT
RETURN
STOP
DOWNFREQRIGHT: B=B-S: SOUND B,D,200,0: SOUND F,D,255,1:
SOUND RESUME: IF B>C THEN GOTO DOWNFREQRIGHT
RETURN
STOP
```

SLEEP EMBODIMENT

Figure 7:
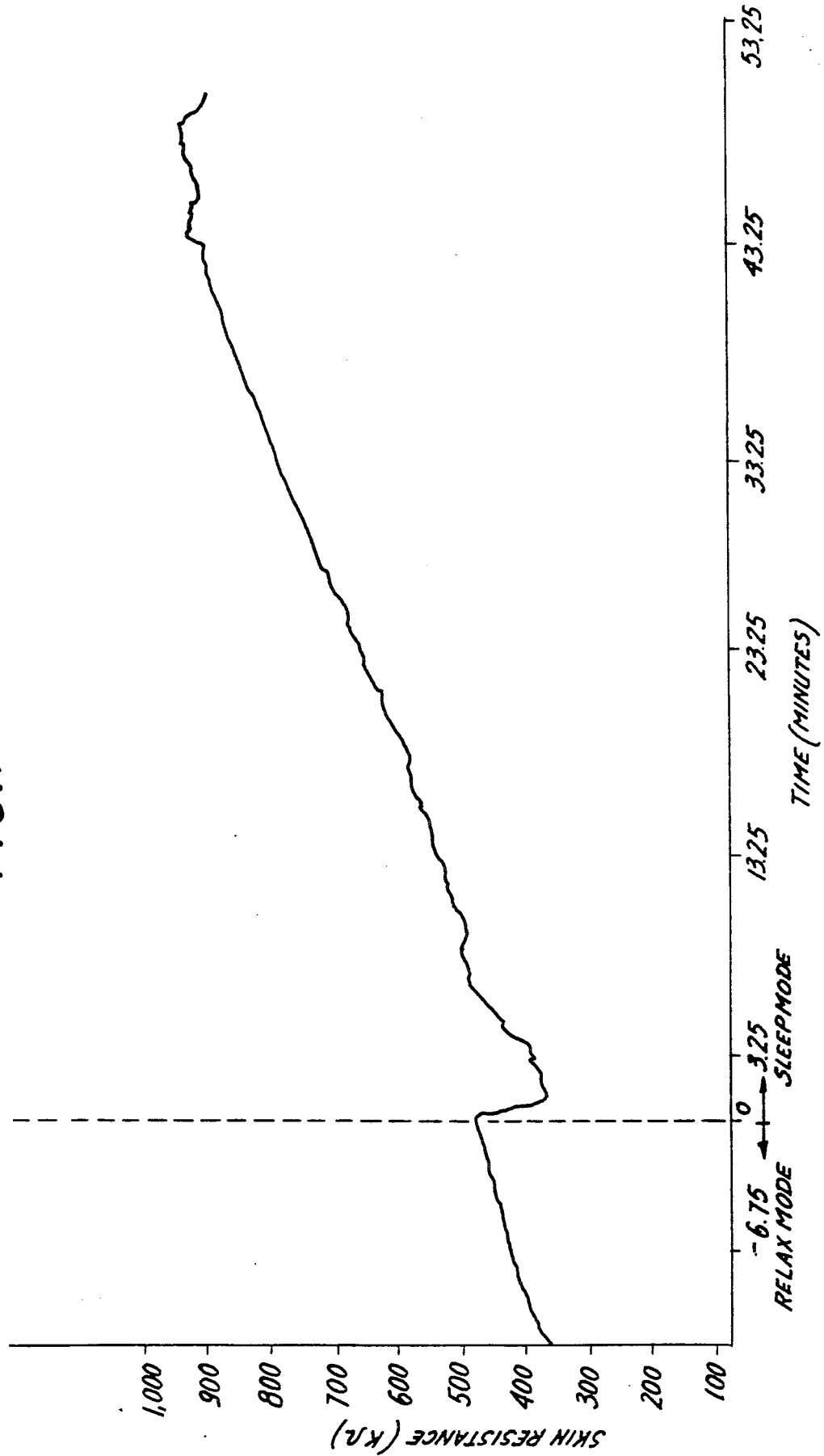
FIG. 7 is a graphical diagram of skin resistance versus time for the SLEEP mode, following the RELAX mode.

The RELAX mode is particularly useful with the SLEEP mode, as shown in FIG. 7. Specifically, the RELAX mode initially relaxes the person and eliminates background information and then the SLEEP mode drives the brain into a deep sleep so that the person can obtain an extremely restful sleep.

In the SLEEP embodiment, an audio signal is supplied to both ears at a frequency which is generally higher than that at which the person is then operating in order to ensure that, upon continuous reduction of the frequency thereof, it will pass through the then operating brain wave frequency of the person.

In the SLEEP embodiment, it is assumed that the brain is operating at a frequency less than 50 Hz. Accordingly, the audio signal supplied to both ears of the person is the same in the SLEEP embodiment and preferably starts at a frequency of 50 Hz. Although this frequency is higher than that at which the person is most probably operating, it is essential that the reduction in frequency pass through the then operating brainwave frequency of the person. Accordingly, the frequency is initially at a value which must be higher than the brain operating frequency of the person. The frequency of the audio signal supplied to both ears is then reduced substantially continuously, preferably in a substantially linear progression over time, for example, to a value of 2 Hz in a time frame of 15 to 20 minutes. The phrase "substantially continuously" refers to a continuous reduction in frequency or in such minute amounts that it is detected by the brain as continuous. By being supplied to both ears, both hemispheres are synchronized for sleep.

Figure 4:
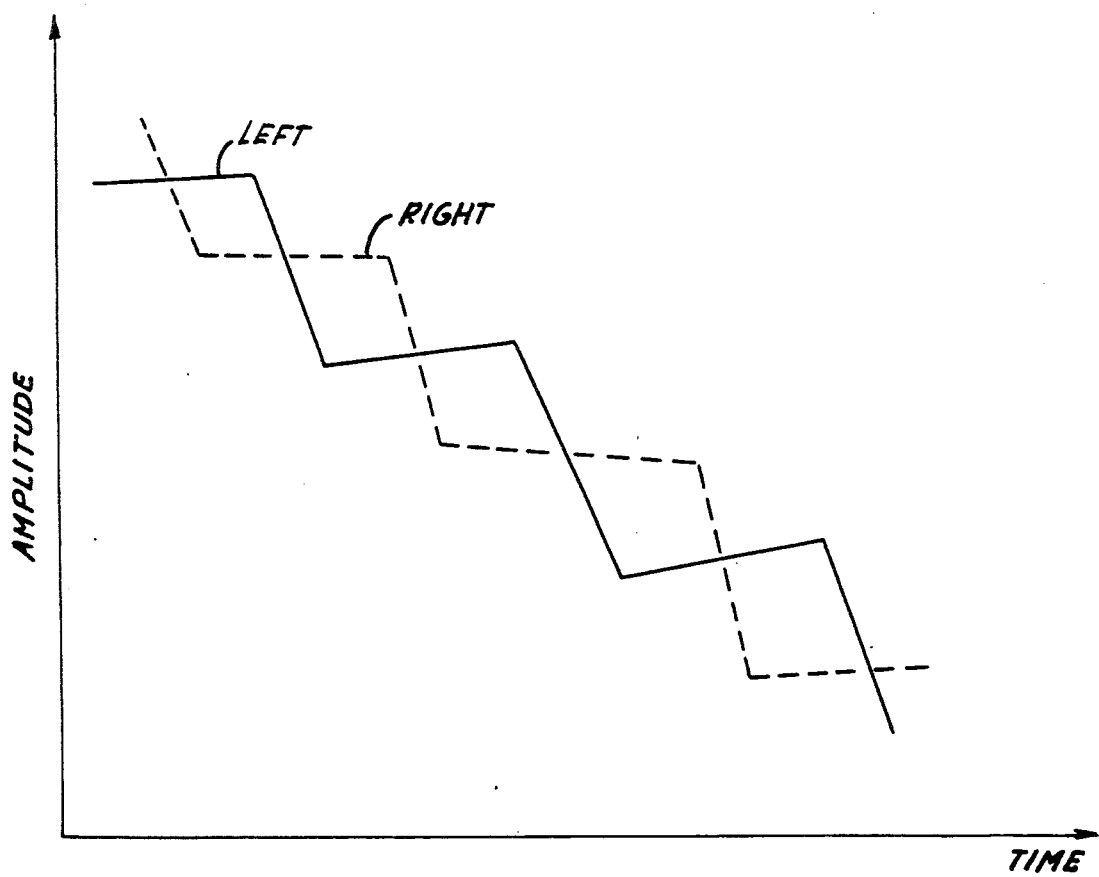
FIG. 4 is a graphical diagram of amplitude versus time for the SLEEP mode.

With respect to the absolute amplitude of the audio signal, the amplitude is started as high a volume as possible, for example, greater than 60 dB, and reduces down to a white noise or zero signal level over a 15 to 20 minute period. At the same time, amplitude modulation is provided between the audio signal supplied to the different ears, in a continuously varying or random manner. Specifically, the varying or amplitude modulation is provided to retain the attention of the person. If a rhythmic sound was produced, the brain would eventually ignore such sound, that is, the sounds would fade into a background. Accordingly, a varying amplitude modulation is provided, which produces a side-to-side variation of the audio sound, whereby the brain goes into a tracking mode, for example, as if it were tracking an article flying through the air. This is the same reason for producing the high amplitude initially, that is, as a startle reflex, to get the attention of the brain and thereby to produce a high level or priority interrupt. One example of amplitude modulation that can be used with this embodiment is shown in FIG. 4.

Figure 5:
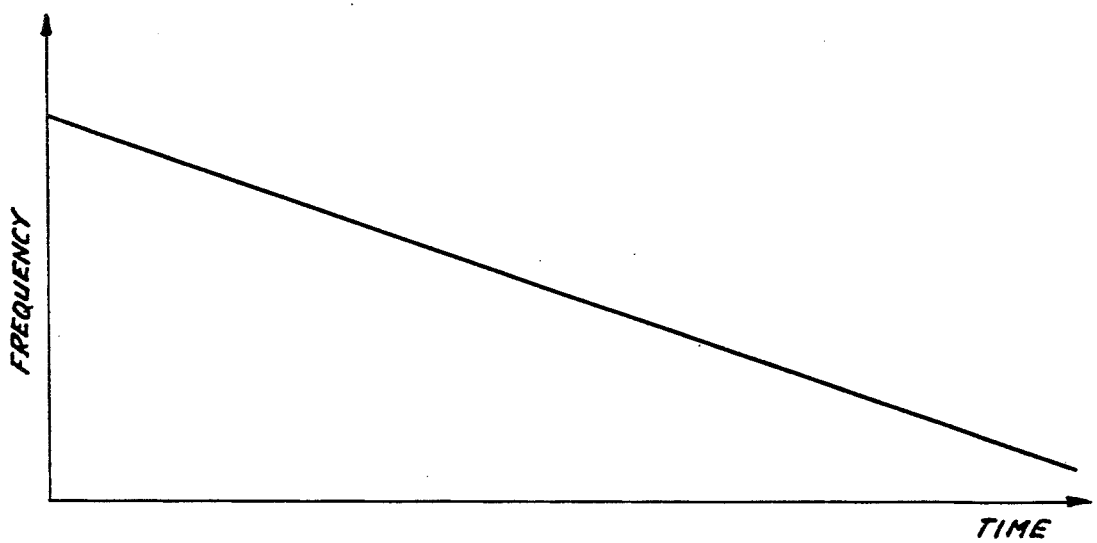
FIG. 5 is a graphical diagram of frequency versus time for the SLEEP mode.
Figure 6:
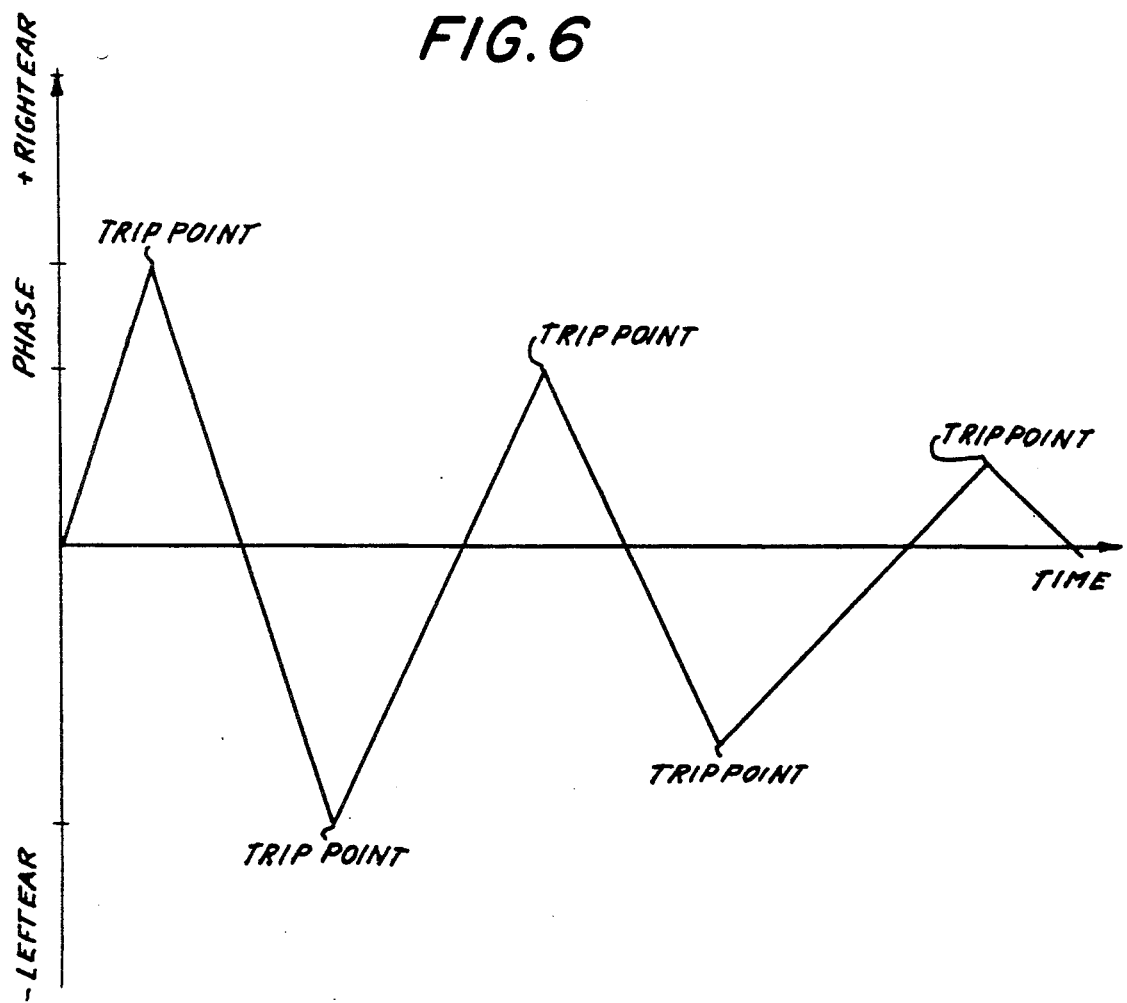
FIG. 6 is a graphical diagram of phase versus time for the SLEEP mode.

Further, the audio signals supplied to the two ears are preferably phase modulated with respect to each other, that is, there is a variable time delay between the signals. The phase modulation is more important than amplitude modulation for side-to-side variation in order to maintain tracking or attention of the brain. As a result, a phase or time delay in microseconds is applied between the signals to each ear. Examples of the variation of frequency and phase over time in this embodiment are shown in FIGS. 5 and 6, respectively.

It will be appreciated that the present invention is very different from prior art methods in which an audio signal of a constant fixed frequency is supplied to the ears of a person, such constant frequency being lower than that of the then operating frequency of the person in order to urge the brain to the lower frequency by a brute-force method. The present invention, rather, is believed to phase lock onto the brain wave frequency of the person and to gently carry the same down to the desired sleep frequency. The scanning or continuously varying frequency is believed to be important since the different halves generally operate at different brain frequencies. This is because one brain half is generally dominant over the other brain half. Therefore, by scanning at different frequencies from a higher frequency to a lower frequency, each brain half is locked onto the respective frequency and carried down so that both brain halves are operating synchronously with each other and are moved to the lower frequency brain wave pattern corresponding to the sleep state.

Tests have been performed to verify the results achieved with the present invention. Specifically, skin resistance to electrical current is a test that has been approved, for example, in the aforementioned Scientific American article. As stated therein, during meditation, skin resistance to an electrical current increases markedly. It has been found that skin resistance increases markedly with the present invention, as shown in FIG. 7, in which the SLEEP embodiment follows a thirty-two minute application of the RELAX embodiment.

It will be appreciated that the audio signal can be generated and applied in different ways. For example, the audio signal can be recorded on an audio tape and played back through headphones connected with a conventional tape cassette player. Alternatively, the audio signals can be applied through electronic circuitry to headphones or to a hearing-aid type device. Still further, the audio signal can be computer generated.

Figure 8:
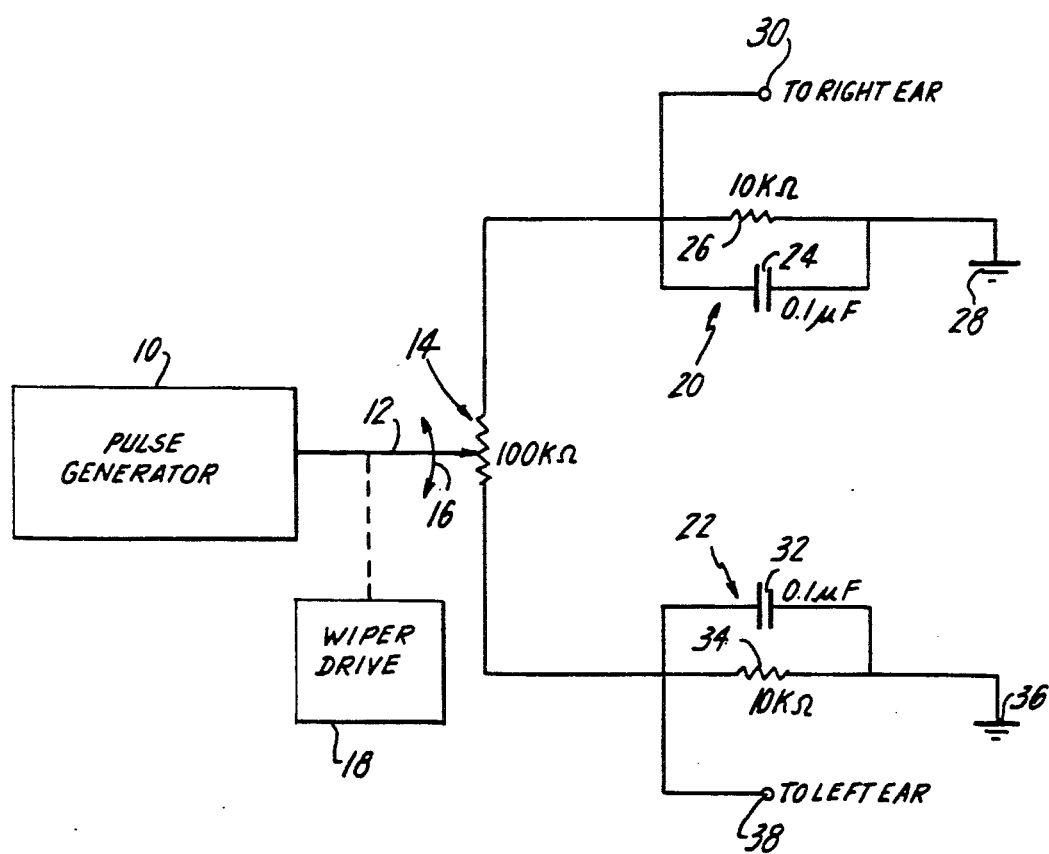
FIG. 8 is a block-circuit wiring diagram for producing audio signals for the SLEEP mode.

Referring now to FIG. 8, one embodiment of circuitry that can be utilized for producing the audio signals will now be described. As shown, a pulse generator 10 supplies a pulse signal to a wiper arm 12 of a potentiometer 14. Wiper arm 12 is continuously moved up and down in the direction of double-headed arrow 16 by a wiper drive 18. As a result, the amplitude is varied between the right ear and the left ear. In order to vary the phase of the signals applied to each ear, an RC circuit 20 is connected to one end of potentiometer 14 and an RC circuit 22 is connected to the opposite end of potentiometer 14. RC circuit 20 includes a capacitor 24 connected in parallel with a resistor 26, with this arrangement of RC circuit 20 being connected in series between the one output of potentiometer 14 and ground 28. The output terminal 30 to the right ear is connected between RC circuit 20 and potentiometer 14. In like manner, RC circuit 22 includes a capacitor 32 and resistor 34 connected in parallel with each other. This arrangement of RC circuit 22 is connected between the other end of potentiometer 14 and ground 36, and the output terminal 38 for the left ear is connected between potentiometer 14 and RC circuit 22. The phase can be varied by changing the resistor values of resistors 26 and 34 in the respective circuits, thereby changing the RC time constant. Therefore, as wiper arm 12 is moved in the direction of arrow 16, the phase and amplitude of the output audio signals change in accordance with the teachings above.

Thus, with the circuit of FIG. 8, the frequency of the audio signals is substantially continuously varied by pulse generator 10 in a range of approximately 0–60 Hz and in a substantially identical manner. Such variation occurs only in a first direction, that is, from a high frequency to a low frequency in the SLEEP embodiment and from a low frequency to a high frequency in the UP embodiment.

In addition, in order to maintain the attention span of the brain during such frequency variation, the signal is further varied so that the person perceives the signal moving back and forth between the left and right ears. Thus, potentiometer 14 with wiper drive 18 provides a relative amplitude variation between the left and right audio signals so that the person perceives the signal moving back and forth between the left and right ears. In like manner, and in combination with potentiometer 14, RC circuits 20 and 22 provide a relative time delay or phase shift between the left and right audio signals so that, again, the person perceives the audio signal moving back and forth between the left and right ears.

It will be appreciated that, in the SLEEP and UP embodiments, the frequency range is varied only in the range of approximately 0–60 Hz. This is below the normal frequency variation of musical selections.

Further, it will be appreciated that, for low frequencies of this nature, the time delay or phase difference between the left and right signals produces a greater effect than the relative amplitude in order to make the brain perceive a movement of the signal back and forth between the left and right ears.

Figure 9:
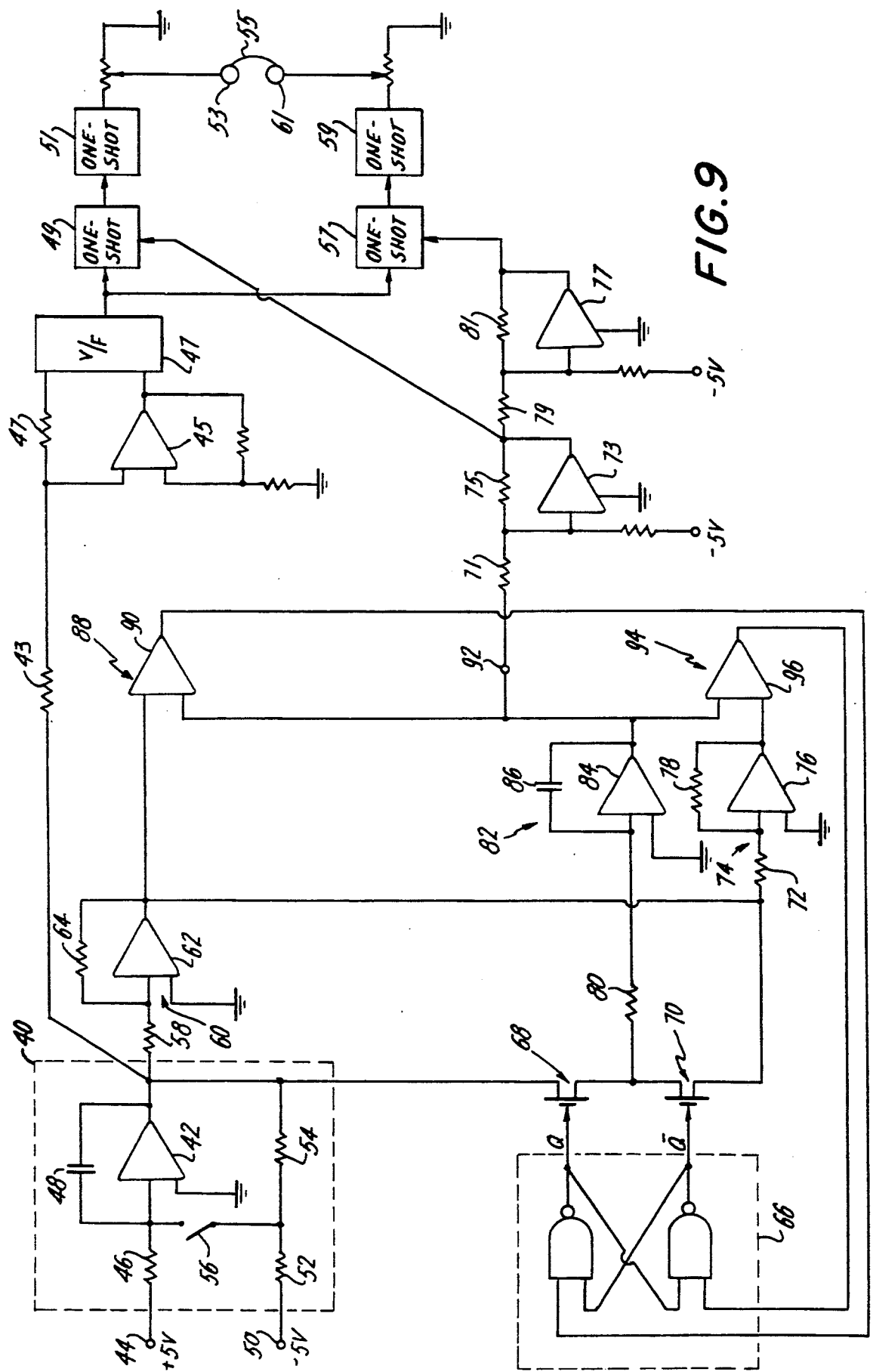
FIG. 9 is another block-circuit wiring diagram for producing audio signals for the SLEEP mode.

Referring now to FIG. 9, an alternate embodiment of circuitry for producing the necessary audio signals in the sleep embodiment will now be described. As shown, a control integrator 40 is provided which produces the reduction in frequency shown in FIG. 5. In addition, control integrator 40 moves the trip points in, as shown in FIG. 6, with the passage of time. Specifically, control integrator 40 includes an amplifier 42 having one input connected to ground and its other input connected to a positive voltage terminal 44 supplied with +5V, through a resistor 46. A capacitor 48 is connected in parallel with amplifier 42. In addition, a negative supply terminal 50, supplied with −5V, is connected to the output of amplifier 42 through two series connected resistors 52 and 54. The connection point between resistors 52 and 54 is connected to the positive input of amplifier 42 through a switch 56. The output of amplifier 42 is connected through a resistor 58 to an invertor 60 comprised of an amplifier 62 having a feedback resistor 64.

In addition, a RS flip-flop 66 is provided, with its Q output being connected to the input of a FET 68 and its Q-not output being connected to a FET 70. The output of FET 68 is connected to the output of amplifier 42 so as to change the polarity on integrator 40 in accordance with switching of FETs 68 and 70.

The output electrode of FET 70 is connected through a resistor 72 to an invertor 74 comprised of an amplifier 76 and feedback resistor 78. In addition, the commonly-connected electrodes of FETs 68 and 70 are connected through a resistor 80 to the input of a main integrator 82 that produces the slopes shown in FIG. 6. Main integrator 82 includes an amplifier 84 and a capacitor 86 connected in parallel thereto.

A positive trip comparator 88 comprised of an amplifier 90 has one input connected to the output of invertor 60 and its other input connected to a terminal 92 of the circuit. In like manner, the output of invertor 74 is connected to one input of a negative trip comparator 94 comprised of an amplifier 96 having one input connected to the output of invertor 74 and its other input connected to terminal 92. The output of main integrator 82 is also connected to output terminal 92, and thereby, to positive and negative trip comparators 88 and 94, respectively.

Positive trip comparator 88 resets RS flip-flop 66 to change the polarity of the output signal, as shown in FIG. 3, when the signal supplied thereto reaches +5V. In like manner, negative trip comparator 94 functions to reset flip-flop 66 to change the polarity of the output signal when the signal supplied thereto from invertor 74 reaches −5V. Accordingly, the direction of the phase of the output signal changes at the various trip points in accordance with the operation of trip comparators 88 and 94, with the slope of the output signal being changed by main integrator 82 and with the frequency varying in accordance with the output from control integrator 40.

With the circuitry thus far described in FIG. 9, the output of control integrator 40 at the output of amplifier 42 constitutes the main frequency control voltage which controls the voltage in the manner shown in FIG. 5, while the signal at terminal 92 constitutes the left/right phasing signal which controls the phase between the left and right channels in accordance with the diagram of FIG. 6.

The main frequency control voltage from amplifier 42 is therefore further supplied through a first resistor 43 to one input of an amplifier 45 and also from said input of amplifier 45 through another resistor 47 to a voltage-to-frequency (V/F) convertor 47, the output of which is supplied through two series-connected one-shots 49 and 51 which supply an output signal to the left ear 53 of headphones 55. In like manner, the output of V/F convertor 47 is supplied through two series connected one-shots 57 and 59, with the output of one-shot 59 supplying the output signal to the right ear 61 of headphones 55. As a result, one-shots 49, 51 produce a first delay to left ear 53, while one-shots 57, 59 supply a second delay to right ear 61.

In order to adjust the voltage to set the respective delay times to produce the left/right phasing shown in FIG. 6, the signal at terminal 92 is supplied through a first resistor 71 to an amplifier 73 having a feedback resistor 75. The output of amplifier 73 is supplied to one-shot 49 to adjust the voltage so as to set the delay time thereof. In like manner, the output of amplifier 73 is supplied through another resistor 79 to the input of an amplifier 77 having a feedback resistor 81, with the output of amplifier 77 being supplied to one-shot 57 to adjust the voltage thereof so as to set the delay. In this manner, both the frequency and the phase are continuously adjusted in accordance with FIGS. 5 and 6.

Thus, with the embodiment of FIG. 9, integrator 40 provides a main frequency control voltage for substantially continuously varying the frequency of both of the first and second audio signals only in a first direction, that is, from a high frequency to a low frequency in the SLEEP embodiment and from a low frequency to a high frequency in the UP embodiment. The variation of the first and second audio signals in the SLEEP and UP embodiments is in a substantially identical manner and in the range of approximately 0–60 Hz.

Further, in the embodiment of FIG. 9, a phase variation is provided between the left and right audio signals. Specifically, this is provided by one-shots 49, 51, 57 and 59, and the circuitry which provides the control of the delay of one-shots 49 and 57. As a result, because of such phase variation, the person perceives the audio signal moving back and forth between the left and right ears.

UP EMBODIMENT

Figure 11:
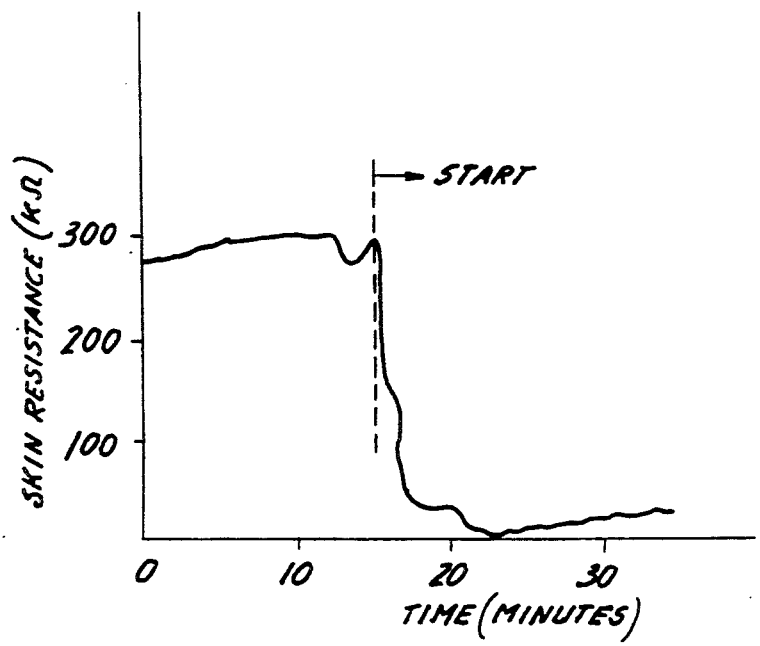
FIG. 11 is a graphical diagram of skin resistance versus time for the UP mode.

The third embodiment, which is termed the UP or enhancement embodiment, is the opposite of the SLEEP embodiment. Specifically, in the UP embodiment, the person is already awake. However, the frequency of the brain waves is not sufficiently high. Accordingly, it is necessary to raise the brain wave frequency, and particularly, to increase the performance of the person, for example, in sporting events, as shown, for example, in FIG. 11. It has been found, for example, with the UP embodiment that performance at a sporting event, such as a tennis match, is improved remarkably. It is believed that during a tennis match this increased performance results from the brain being able to follow the tennis ball better and see the ball earlier so as to provide more time for the player to prepare for and hit the ball.

In a preferred mode of the UP embodiment, both ears of the person are supplied with the same audio signal having a substantially continuously varying frequency which varies, for example, from 20 Hz to 40 Hz, although the signals are amplitude and/or phase modulated. It is believed that, if the brain wave frequency of the person is less than 20 Hz, the brain will phase lock onto audio signals of the same frequency or multiples of the same frequency. Thus, even if the brain is operating at a 10 Hz frequency rate, when an audio signal of 20 Hz is supplied, the brain will be phase locked onto such a signal and will be nudged up as the frequency is increased. Without such variation in frequency of the audio signal, the brain wave frequency will phase lock thereto, but will not be nudged up. Preferably, the audio signal changes from 20 Hz to 40 Hz in a time period of approximately 5 minutes and continuously repeats thereafter so as to nudge the brain frequency to a higher frequency during each cycle.

It is believed that, by starting the audio frequency at a lower frequency below 20 Hz, the brain cannot initially lock onto such frequency since it is too slow and the attention span cannot be maintained. Thus, for example, during the first 5 minute cycle, the brain frequency of 10 Hz may be nudged to 11 Hz. Thereafter, the brain will lock onto a frequency of an integral multiple thereof, that is, 22 Hz so that the brain is nudged up to, for example, 13 Hz and so on. In other words, the brain locks onto an integral multiple, greater than or equal to one, of the brain frequency. It is to be noted, however, that in most applications, the brain wave frequency will initially be in the Alpha region, and the UP embodiment raises the brain frequency to the Beta region.

Figure 10:
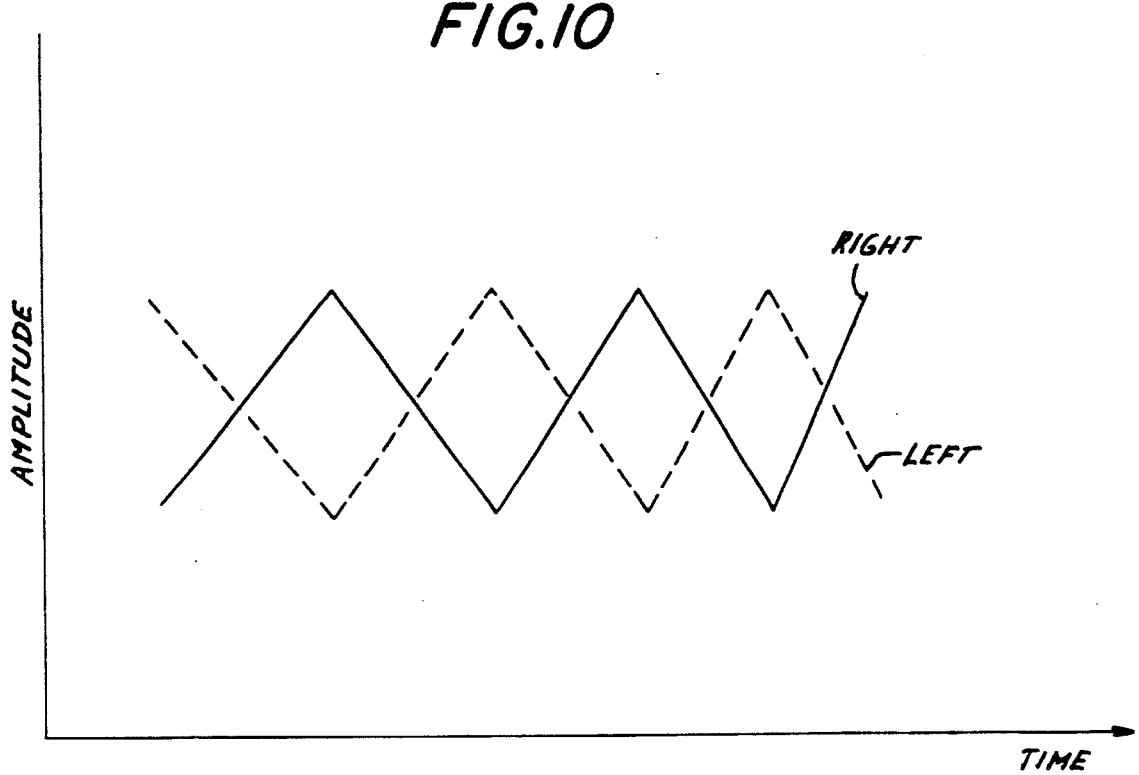
FIG. 10 is a graphical diagram of amplitude versus time for the UP mode.

With the UP embodiment, the amplitude is maintained constant, preferably always at a level greater than 60 dB, since the attention of the brain must always be maintained, as shown in FIG. 10. However, although the absolute amplitude is maintained the same, there is still amplitude modulation or variation between the left and right ears, as shown in FIG. 10. It will be appreciated that the amplitude modulation increases with time in the UP embodiment, whereas, in the SLEEP embodiment, such amplitude modulation reduces with time. Accordingly, because of such amplitude variation, there is an apparent angle of amplitude for the sound source which varies between +90 degrees and −90 degrees, corresponding to a total right ear sound and a total left ear sound. In other words, there is a frequency of apparent angle change, whereas the degrees/second changes.

In addition, there is a phase modulation which is identical to the down embodiment of FIG. 6. However, the change between the phase lag and the phase lead is greater in the UP embodiment than in the SLEEP embodiment. Accordingly, the phase modulation forces the person to scan, as if watching a ball go back and forth. It is noted that, if the phase modulation is too fast, the brain cannot track or follow the same. Therefore, the phase modulation may have to be adjusted for the particular person.

Accordingly, it will be appreciated that the amplitude, amplitude modulation and phase modulation can vary with either the SLEEP embodiment or the UP embodiment.

In order to produce the audio signals for the UP embodiment, the circuitry of FIGS. 8 and 9 can be utilized. Alternatively, audio tapes can be utilized or the sounds can be computer generated.

Having described specific preferred embodiments of the invention with reference to the accompanying drawings, it will be appreciated that the present invention is not limited to those precise embodiments, and that various changes and modifications can be effected therein by one of ordinary skill in the art without departing from the spirit or scope of the invention as defined by the appended claims.

I claim:

1. Apparatus for varying the brain state of a person, comprising:
    means for producing a first audio signal to be supplied to one ear of the person;
    means for producing a second audio signal to be supplied to the other ear of the person;
    means for substantially continuously varying the frequency of both of said first and second audio signals only in a first direction in a range of approximately 0–60 Hz and in a substantially identical manner, so as to vary the brain state of the person; and
    amplitude varying means for relatively varying the amplitude between said first and second audio signals such that said first and second audio signals are provided with different amplitudes substantially at all times so that the person perceives a moving sound.

2. Apparatus according to claim 1, wherein said means for substantially continuously varying includes a pulse generator.

3. Apparatus according to claim 1, wherein said means for substantially continuously varying includes an integrator.

4. Apparatus according to claim 1, wherein said amplitude varying means includes a potentiometer having a movable wiper arm, one end of said potentiometer being connected to said means for producing a first audio signal and the opposite end of said potentiometer being connected to said means for producing a second audio signal, and drive means for moving said wiper arm in a reciprocating manner along said potentiometer.

5. Apparatus according to claim 1, wherein said first direction is from a first frequency to a second, lower frequency.

6. Apparatus according to claim 5, wherein said first frequency is in the range of 30 Hz to 60 Hz and said second frequency is in the range of 0 Hz to 10 Hz.

7. Apparatus according to claim 6, wherein said first frequency is 50 Hz and said second frequency is 2 Hz.

8. Apparatus for varying the brain state of a person, comprising:
    means for producing a first audio signal to be supplied to one ear of the person;
    means for producing a second audio signal to be supplied to the other ear of the person;
    means for substantially continuously varying the frequency of both of said first and second audio signals only in a first direction in a range of approximately 0–60 Hz and in a substantially identical manner, so as to vary the brain state of the person; and
    phase varying means for varying the phase between said first and second audio signals such that the person perceives a moving sound.

9. Apparatus according to claim 8, wherein said phase varying means includes time delay means for imparting a relative time delay between said first and second audio signals.

10. Apparatus according to claim 9, wherein said time delay means includes first time delay circuit mean for imparting a time delay to said first audio signal and second time delay circuit means for imparting a time delay to said second audio signal.

11. Apparatus according to claim 10, wherein said first and second time delay circuit means each include an RC circuit.

12. Apparatus according to claim 10, wherein said first and second time delay circuit means each include at least one one-shot.

13. Apparatus according to claim 9, wherein said phase varying means includes control means for controlling the relative time delay of said time delay means.

14. Apparatus according to claim 13, wherein said means for controlling includes integrator means for supplying an integrated signal to said time delay means to vary the relative time delay between said first and second audio signals.

15. Apparatus for varying the brain state of a person, comprising:
   means for producing a first audio signal to be supplied to one ear of the person;
   means for producing a second audio signal to be supplied to the other ear of the person;
   means for substantially continuously varying the frequency of both of said first and second audio signals only in a first direction from a first frequency to a second, higher frequency in a range of approximately 0–60 Hz and in a substantially identical manner, so as to vary the brain state of the person.

16. Apparatus according to claim 15, wherein said first frequency is in the range of approximately 10 Hz to 20 Hz and said second frequency is in the range of approximately 30 Hz to 50 Hz.

17. Apparatus according to claim 16, wherein said first frequency is approximately 20 Hz and said second frequency is approximately 40 Hz.

18. A method for varying the brain state of a person, comprising the steps of:
   producing a first audio signal supplied to one ear of the person;
   producing a second audio signal supplied to the other ear of the person;
   substantially continuously varying the frequency of both of said first and second audio signals only in a first direction in a range of approximately 0–60 Hz and in a substantially identical manner, so as to vary the brain state of the person; and
   relatively varying the amplitude between said first and second audio signals such that said first and second audio signals are provided with different amplitudes substantially at all times so that the person perceives a moving sound.

19. A method according to claim 18, wherein said step of substantially continuously varying includes the step of substantially continuously varying the frequency of both of said first and second audio signals only in a first direction from a first frequency to a second, lower frequency.

20. A method according to claim 19, wherein said first frequency is in the range of 30 Hz to 60 Hz and said second frequency is in the range of 0 Hz to 10 Hz.

21. A method according to claim 20, wherein said first frequency is 50 Hz and said second frequency is 2 Hz.

22. A method for varying the brain state of a person, comprising the steps of:
   producing a first audio signal supplied to one ear of the person;
   producing a second audio signal supplied to the other ear of the person;
   substantially continuously varying the frequency of both of said first and second audio signals only in a first direction in a range of approximately 0–60 Hz and in a substantially identical manner, so as to vary the brain state of the person; and
   varying the phase between said first and second audio signals such that the person perceives a moving sound.

23. A method according to claim 22, wherein said step of varying the phase includes the step of imparting a relative time delay between said first and second audio signals.

24. A method according to claim 23, wherein said step of imparting a relative time delay includes the steps of imparting a first time delay to said first audio signal and imparting a second time delay to said second audio signal.

25. A method according to claim 23, further including the step of controlling said relative time delay between said first and second audio signals.

26. A method for varying the brain state of a person, comprising the steps of:
   producing a first audio signal supplied to one ear of the person;
   producing a second audio signal supplied to the other ear of the person; and
   substantially continuously varying the frequency of both of said first and second audio signals only in a first direction from a first frequency to a second, higher frequency in a range of approximately 0–60 Hz and in a substantially identical manner, so as to vary the brain state of the person.

27. A method according to claim 26, wherein said first frequency is in the range of approximately 10 Hz to 20 Hz and said second frequency is in the range of approximately 30 Hz to 50 Hz.

28. A method according to claim 27, wherein said first frequency is approximately 20 Hz and said second frequency is approximately 40 Hz.

29. Apparatus for varying the brain state of a person, comprising:
   signal supply means for storing a first frequency signal used to generate a first audio signal to be supplied to one ear of the person, and a second frequency signal used to generate a second audio signal to be supplied to the other ear of the person, such that the frequency of both of said generated first and second audio signals substantially continuously vary only in a first direction in a range of approximately 0–60 Hz and in a substantially identical manner, so as to vary the brain state of the person, and with the amplitude between said first and second audio signals being relatively varied such that said first and second audio signals are provided with different amplitudes substantially at all times so that the person perceives a moving sound; and playback means for generating said first and second audio signals from said first and second frequency signal stored by said signal supply means.

30. Apparatus according to claim 29, wherein said first direction is from a first frequency to a second, lower frequency.

31. Apparatus according to claim 30, wherein said first frequency is in the range of 30 Hz to 60 Hz and said second frequency is in the range of 0 Hz to 10 Hz.

32. Apparatus according to claim 31, wherein said first frequency is 50 Hz and said second frequency is 2 Hz.

33. Apparatus for varying the brain state of a person, comprising:
   signal supply means for storing a first frequency signal used to generate a first audio signal to be supplied to one ear of the person, and a second frequency signal used to generate a second audio signal to be supplied to the other ear of the person, such that the frequency of both of said generated first and second audio signals substantially continuously vary only in a first direction from a first frequency to a second, higher frequency in a range of approximately 0–60 Hz and in a substantially identical manner, so as to vary the brain state of the person; and playback means for generating said first and second audio signals from said first and second frequency signal stored by said signal supply means.

34. Apparatus according to claim 33, wherein said first frequency is in the range of approximately 10 Hz to 20 Hz and said second frequency is in the range of approximately 30 Hz to 50 Hz.

35. Apparatus according to claim 34, wherein said first frequency is approximately 20 Hz and said second frequency is approximately 40 Hz.

36. Apparatus for varying the brain state of a person, comprising:
   means for producing a first audio signal to be supplied to one ear of the person;
   means for producing a second audio signal to be supplied to the other ear of the person; and
   means for substantially continuously varying the frequency of at least one of said first and second audio signals such that said first and second audio signals have different frequencies at substantially all times in order to produce substantially continuously varying binaural beats in the brain of the person when said first and second audio signals are supplied to said first and second ears, respectively.

37. Apparatus according to claim 36, wherein said means for varying includes means for maintaining the frequency of one of said first and second audio signals constant and means for substantially continuously varying the frequency of the other of said first and second audio signals.

38. Apparatus according to claim 37, wherein said means for substantially continuously varying the frequency of the other of the first and second audio signals includes means for substantially continuously reducing the frequency of the other of said first and second audio signals so as to approach the frequency of said one of said first and second audio signals.

39. Apparatus according to claim 36, wherein said means for substantially continuously varying includes:
   (a) means for performing a cycle of:
      i) maintaining the frequency of said first audio signal substantially constant at a predetermined low frequency;
      ii) substantially continuously reducing the frequency of said second audio signal from a high frequency having a first value, toward said low frequency;
      iii) maintaining the frequency of said second audio signal substantially constant at said low frequency, after said second audio signal has decreased to said low frequency;
      iv) substantially continuously varying the frequency of said first audio signal from said high frequency toward said low frequency; and
   (b) means for decreasing said first value of said high frequency by a predetermined value for each cycle until said high frequency substantially equals said low frequency.

40. Apparatus according to claim 39, wherein said first value of said low frequency is substantially 200 Hz, said first value of said high frequency is substantially 230 Hz, and said predetermined value is one, Hz.

41. Apparatus according to claim 36, further including phase varying means for varying the phase between said first and second audio signals such that the person perceives a moving sound.

42. Apparatus according to claim 41, wherein said phase varying means includes time delay means for imparting a relative time delay between said first and second audio signals.

43. Apparatus according to claim 42, wherein said time delay means includes first time delay circuit means for imparting a time delay to said first audio signal and second time delay circuit means for imparting a time delay to said second audio signal.

44. A method for varying the brain state of a person, comprising the steps of:
   producing a first audio signal supplied to one ear of the person;
   producing a second audio signal supplied to the other ear of the person; and
   substantially continuously varying the frequency of at least one of said first and second audio signals such that said first and second audio signals have different frequencies at substantially all times in order to produce substantially continuously varying binaural beats in the brain of the person when said first and second audio signals are supplied to said first and second ears, respectively.

45. A method according to claim 44, wherein said step of varying includes the steps of maintaining the frequency of one of said first and second audio signals constant and substantially continuously varying the frequency of the other of said first and second audio signals.

46. A method according to claim 45, wherein said step of substantially continuously varying the frequency of the other of the first and second audio signals includes the step of substantially continuously reducing the frequency of the other of said first and second audio signals so as to approach the frequency of said one of said first and second audio signals.

47. A method according to claim 44, wherein said step of substantially continuously varying includes the steps of:
   (a) performing a cycle of:
      i) maintaining the frequency of said first audio signal substantially constant at a low frequency;
      ii) substantially continuously varying the frequency of said second audio signal from a high frequency having a first value, toward said low frequency;
      iii) maintaining the frequency of said second audio signal substantially constant at said low frequency, after said second audio signal has decreased to said low frequency;
      iv) substantially continuously varying the frequency of said first audio signal from said high frequency toward said low frequency; and
   (b) decreasing said first value of said high frequency by a predetermined value for each cycle until said high frequency equals said low frequency.

48. A method according to claim 47, wherein said first value of said low frequency is substantially 200 Hz, said first value of said high frequency is substantially 230 Hz, and said predetermined value is one Hz.

49. A method according to claim 44, further including the step of varying the phase between said first and second audio signals such that the person perceives a moving sound.

50. A method according to claim 49, wherein said step of varying the phase includes the step of imparting a relative time delay between said first and second audio signals.

51. A method according to claim 50, wherein said step of imparting a relative time delay includes the steps of imparting a first time delay to said first audio signal and imparting a second time delay to said second audio signal.

52. Apparatus for varying the brain state of a person, comprising:

signal supply means for storing a first frequency signal used to generate a first audio signal to be supplied to one ear of the person, and a second frequency signal used to generate a second audio signal to be supplied to the other ear of the person, such that the frequency of at least one of said first and second audio signals is substantially continuously varied such that said first and second audio signals have different frequencies at substantially all times in order to produce substantially continuously varying binaural beats in the brain of the person when said first and second audio signals are supplied to said first and second ears, respectively, so as to vary the brain state of the person; and playback means for generating said first and second audio signals from said first and second frequency signal stored by said signal supply means.

53. Apparatus according to claim 52, wherein the frequency of one of said first and second audio signals is maintained constant, while the frequency of the other of said first and second audio signals is varied.

54. Apparatus according to claim 53, wherein the frequency of the other of the first and second audio signals is substantially continuously reduced so as to approach the frequency of said one of said first and second audio signals.

55. Apparatus according to claim 52, wherein the phase between said first and second audio signals is varied such that the person perceives a moving sound.

56. Apparatus according to claim 55, wherein there is a relative time delay between said first and second audio signals.

57. Apparatus for varying the brain state of a person, comprising:

signal supply means for storing a first frequency signal used to generate a first audio signal to be supplied to one ear of the person, and a second frequency signal used to generate a second audio signal to be supplied to the other ear of the person, such that the frequency of both of said generated first and second audio signals substantially continuously vary only in a first direction in a range of approximately 0-60 Hz and in a substantially identical manner, so as to vary the brain state of the person, and with the phase between said first and second audio signals being varied such that the person perceives a moving sound; and playback means for generating said first and second audio signals from said first and second frequency signal stored by said signal supply means.

* * * * *